(12) United States Patent
Rabinovici-Cohen et al.

(10) Patent No.: US 11,620,746 B2
(45) Date of Patent: Apr. 4, 2023

(54) MRI ANNOTATION

(71) Applicant: International Business Machines Corporation, Armonk, NY (US)

(72) Inventors: Simona Rabinovici-Cohen, Haifa (IL); Shaked Perek, Givatayim (IL); Tal Tlusty Shapiro, Zichron Yaakov (IL); Dana Levanony, Tel Aviv (IL); Efrat Hexter, Beit Shemesh (IL); Ami Abutbul, Qiryat Gat (IL)

(73) Assignee: International Business Machines Corporation, Armonk, NY (US)

( * ) Notice: Subject to any disclaimer, the term of this patent is extended or adjusted under 35 U.S.C. 154(b) by 169 days.

(21) Appl. No.: 17/093,904

(22) Filed: Nov. 10, 2020

(65) Prior Publication Data

US 2022/0148159 A1 May 12, 2022

(51) Int. Cl.
*G06T 7/00* (2017.01)
*G16H 30/20* (2018.01)
(Continued)

(52) U.S. Cl.
CPC ............ *G06T 7/0012* (2013.01); *A61B 5/055* (2013.01); *G01R 33/4835* (2013.01);
(Continued)

(58) Field of Classification Search
None
See application file for complete search history.

(56) References Cited

U.S. PATENT DOCUMENTS 7,828,732 B2    11/2010   Wang
2012/0256920 A1*  10/2012  Marshall .............. A61B 6/0414
                                                  345/420
(Continued)

FOREIGN PATENT DOCUMENTS

WO    WO-2011123097 A1 *  10/2011   ............... G06F 1/26
WO    WO-2011132097 A2 *  10/2011   ......... G06F 16/3331
(Continued)

OTHER PUBLICATIONS

Yang S-N, Li F-J, Liao Y-H, Chen Y-S, Shen W-C, Huang T-C (2015) Identification of Breast Cancer Using Integrated Information from MRI and Mammography. PLoS ONE 10(6): e0128404. doi:10.1371/journal.pone.0128404 (Year: 2015).*
(Continued)

*Primary Examiner* — Vu Le
*Assistant Examiner* — Courtney Joan Nelson
(74) *Attorney, Agent, or Firm* — Edward J. Wixted, III

(57) ABSTRACT

Embodiments herein disclose computer-implemented methods, computer program products and computer systems for annotating magnetic resonance imaging (MRI) images. The method may include receiving mammogram (MG) image data representing annotated MG images of a patient breast, the annotated MG images being one of either a craniocaudal view or of a mediolateral oblique view. The method may include identifying annotations representing an abnormality at a first location in the annotated MG images; receiving MRI image data representing MRI images of the patient breast; generating annotated MRI image data using the MRI image data and the annotations identified in the annotated MG images, the annotated MRI image data including MRI annotations at a second location based at least in part on the first location, the MRI annotations in the annotated MRI
(Continued)

image data representing the abnormality; and storing the annotated MRI image data in a database.

18 Claims, 8 Drawing Sheets

(51) Int. Cl.
    *G16H 50/20*     (2018.01)
    *G06N 20/00*     (2019.01)
    *A61B 5/055*     (2006.01)
    *G01R 33/483*     (2006.01)
    *G01R 33/56*     (2006.01)

(52) U.S. Cl.
    CPC ......... *G01R 33/5608* (2013.01); *G06N 20/00* (2019.01); *G16H 30/20* (2018.01); *G16H 50/20* (2018.01); *G06T 2207/10088* (2013.01); *G06T 2207/30068* (2013.01)

(56) References Cited

U.S. PATENT DOCUMENTS

| | | |
|---|---|---|
| 2014/0348404 A1 | 11/2014 | Jerebko |
| 2018/0033143 A1 | 2/2018 | Buelow |
| 2020/0226368 A1* | 7/2020 | Bakalo ............... G06K 9/00536 |

FOREIGN PATENT DOCUMENTS

| | | | | |
|---|---|---|---|---|
| WO | WO-2017211910 A1 * | 12/2017 | ........... | A61B 8/0825 |
| WO | 2019091807 A1 | 5/2019 | | |
| WO | WO-2020068851 A1 * | 4/2020 | ........... | A61B 5/0035 |

OTHER PUBLICATIONS

Hopp et al., "Automatic multimodal 2D/3D breast image registration using biomechanical FEM models and intensity-based optimization", Medical Image Analysis, vol. 17, Issue 2, pp. 209-218, Feb. 2013, 10 Pages.

Liao et al., "Multiview 2D/3D Rigid Registration via a Point-Of-Interest Network for Tracking and Triangulation", IEEE/CVF Conference on Computer Vision and Pattern Recognition (CVPR), pp. 12630-12639, doi: 10.1109/CVPR.2019.01292, Long Beach, CA, USA, 2019, 10 Pages.

Mclaughlin et al., "Intensity-based Registration versus Feature-based Registration for Neurointerventions", ResearchGate, United Kingdom, Jan. 2001, 5 Pages.

Pathmanathan et al., "Predicting Tumor Location by Modeling the Deformation of the Breast", IEEE Transactions On Biomedical Engineering, vol. 55, No. 10, Oct. 2008, 10 Pages.

Rugma et al., "Positioning Lesion from Breast MRI and Mammogram using Registration Method", International Journal of Engineering Research & Technology (IJERT), ISSN: 2278-0181, vol. 3, Issue 5, May 2014, 6 Pages.

Sinha et al., "Multi-modality 3D breast imaging with X-Ray tomosynthesis and automated ultrasound", Proceedings of the 29th Annual International Conference of the IEEE EMBS Cité Internationale, Lyon, France, Aug. 23-26, 2007, 4 Pages.

International Search Report and Written Opinion, dated Jul. 13, 2022, from International Application No. GB2115058.6, filed Oct. 21, 2021, IBM, 3 pages.

International Search Report and Written Opinion, dated Mar. 7, 2022, from International Application No. GB2115058.6, filed Oct. 21, 2021, IBM, 6 pages.

\* cited by examiner

MRI ANNOTATION

BACKGROUND

The present invention relates generally to the field of medical image annotation, and more particularly to projecting mammogram (MG) image annotations onto magnetic resonance imaging (MRI) images.

In performing breast cancer screening examinations on patients, a medical professional captures and reviews multiple images taken from different viewpoints and from different points in time to make a diagnosis. Medical professionals use mammograms to help to identify early signs of breast cancer. A mammogram is an X-ray picture of the breast and can be used as a screening mammogram to check for breast cancer in women who have no signs or symptoms of the disease. To assist with making a diagnosis, computer-aided diagnosis (CAD) algorithms are often used to make decisions based on single images. Images taken during a mammogram may include different viewpoints or angles for the left breast and for the right breast. For example, standard mammogram image view types may include bilateral craniocaudal (CC), bilateral mediolateral oblique (MLO), wherein bilateral refers to the left and right versions of a view.

Mammography is the more common and cost-effective image diagnosis for performing a breast cancer diagnosis but is limited in not being able to identify all types of abnormalities, especially with hard tissue identifications. Whereas, MRIs are able to identify abnormalities that would be less apparent in a MG examination, although MRIs are more expensive computationally, time consuming, and require higher skill levels.

SUMMARY

The present invention is described in various embodiments disclosing methods, computer program products, and computer systems for annotating magnetic resonance imaging (MRI) images using mammogram annotations. One embodiment of the present disclosure is a computer-implemented method for annotating MRI images, the computer-implemented method may be executed by one or more processors configured for receiving mammogram (MG) image data representing one or more annotated MG images of a patient breast; identifying one or more annotations in the one or more annotated MG images, the one or more annotations representing an abnormality at a first location in the one or more annotated MG images; receiving MRI image data representing one or more MRI images of the patient breast; generating annotated MRI image data using the MRI image data and the one or more annotations identified in the one or more annotated MG images, the annotated MRI image data including one or more annotations representing the abnormality at a second location based at least in part on the first location and storing the annotated MRI image data in a database.

In an embodiment, each of the one or more annotated MG images is one or either a craniocaudal (CC) view or of a mediolateral oblique (MLO) view. The one or more MRI images may include a plurality of image slices including one or more image slices having the abnormality.

Some embodiments may include one or more processors configured for determining a breast side and a quadrant of the patient breast based on the first location in the one or more annotated MG images and locating the corresponding breast side and quadrant in the plurality of image slices of the one or more MRI images. Further, the one or more processors configured for generating the annotated MRI image data may be further configured for mapping the one or more annotations to the second location of the corresponding breast side and quadrant of the MRI images represented in the MRI image data. Furthermore, the one or more processors may be configured for providing the annotated MRI image data to a supervised machine learning model and processing the annotated MRI image data with the one or more annotations using the supervised machine learning model to generate output data corresponding to a diagnosis.

DETAILED DESCRIPTION

Figure 1:
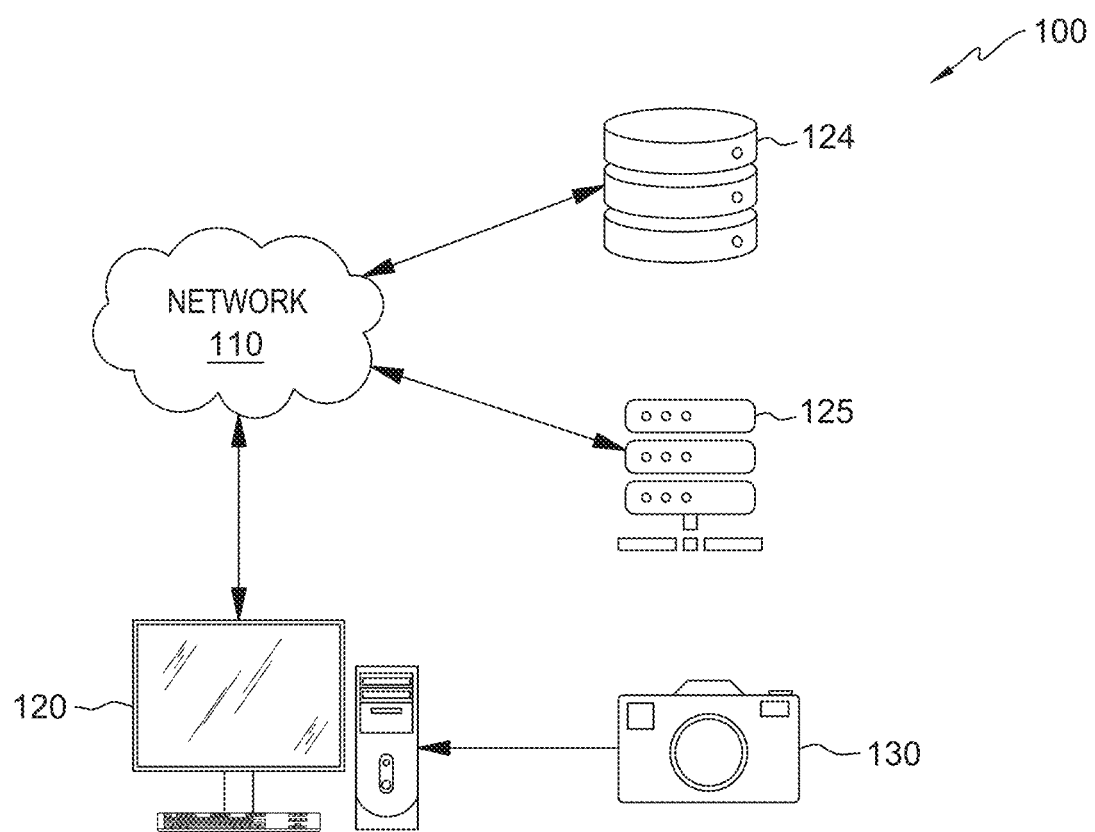
FIG. 1 depicts a block diagram of a distributed data processing environment for annotating MRI images, in accordance with an embodiment of the present invention.

The present invention addresses the problem of efficiently annotating MRI images. When mammographers screen patients for breast cancer, they review multiple images taken from different viewpoints at one or more prior exams before arriving at their diagnosis. A medical professional performing a breast cancer screening exam may capture x-ray images called screening MGs. The screening MG images may be annotated by the medical professional to identify relevant findings (e.g., abnormalities, lesions, tumors) in the images or to show useful information about the relevant findings. The annotations may be saved within the MG image or saved elsewhere and associated with the MG image.

The present invention therefore provides a computer-implemented method to efficiently and automatically annotate MRI images using annotated MG images. During implementation, a computing device comprising one or more processors may be configured to receive MG image data representing one or more annotated MG images of a patient breast from a database.

Each of the one or more annotated MG images is one of either a craniocaudal (CC) view or of a mediolateral oblique (MLO) view. Each image taken during a MG includes a corresponding type of view. For example, a type of view for an image may include a standard type of view or a non-standard type of view for mammograms, in which the standard types of view are generally captured during a screening exam and the non-standard types of views are generally captured in a follow-up diagnostic exam. A standard type of view may be captured during a screening exam and may include a bilateral CC view or a bilateral MLO view, wherein a bilateral type of view may include a positional variant representing the left (L) or right (R) position, indicated as CC L view, CC R view, MLO L view and MLO R view. A non-standard type of view may be captured during a diagnostic exam and may include one of a mediolateral (ML) view, a lateromedial (LM) view, a lateromedial oblique (LMO) view, a late mediolateral (late ML) view, a step oblique (SO) view, a spot view, a spot compression view, a double spot compression view, a magnificent view, an exaggerated craniocaudal view (XCC), an axillary view, a cleavage view, a tangential view, a CC view, a bullseye CC view, a rolled CC view, an elevated CC view, a 20° oblique view, an inferomedial superolateral oblique projection view, and an Eklund technique view. The non-standard images may correspond to the standard images such that the non-standard images may be a variation of one or more of the standard images.

The one or more MRI images may include a plurality of image slices including one or more image slices having an abnormality. In an embodiment, the one or more processors may be configured to apply a lesion segmentation algorithm using only the found relevant image slices and area identified as having the abnormality.

The one or more processors may be configured to identify one or more annotations representing an abnormality at a first location in the one or more annotated MG images and to receive MRI image data representing MRI images of the patient breast.

The one or more processors may be configured to generate annotated MRI image data using the MRI image data and the one or more annotations identified in the one or more annotated MG images. The annotated MRI image data may include the one or more annotations representing the abnormality at a second location based at least in part on the first location.

The one or more processors configured for generating the annotated MRI image data may be further configured for mapping the one or more annotations to the second location of the corresponding breast side and quadrant of the MRI images represented in the MRI image data. For example, the patient breast may be identified by a breast side and a quadrant where the abnormality can be found.

The one or more processors may be configured to store the annotated MRI image data in a database, according to methods of storing data in a database known to those of ordinary skill in the art.

The one or more processors may be configured to provide the annotated MRI image data to a supervised machine learning model and process the annotated MRI image data with the one or more annotations using the supervised machine learning model to generate output data corresponding to a diagnosis.

Embodiments of the present invention provide a system and method for processing MG image data from a standard set of images and/or a diagnostic set of images to determine a diagnostic assessment using a study-level image classifier and a diagnosis model.

Embodiments of the present invention provide a study-level image classifier for processing a standard set and/or diagnostic set of mammograms to determine a classification (e.g., benign, malignant, normal) for each image in the study and produce model output data as a feature vector for each image. A study-level image classifier may include a deep convolutional neural network ("CNN") for image classification, which may be a rule-based machine learning model that combines a discovery component (e.g., genetic algorithm) with a learning component (e.g., supervised learning or unsupervised learning). In general, image classifier systems seek to identify a set of context-dependent rules that collectively store and apply knowledge in a piecewise manner in order to make predictions (e.g., behavior modeling, classification, data mining, regression, function approximation, or game strategy). The study-level image classifier may also include a combination network component configured to concatenate the model output data feature vectors to produce a study-level classification through a series of fully connected layers. The study-level image classifier may be trained using other images tagged with medical labels or associated with annotations and/or diagnostic reports to improve the functionality and accuracy of the image classifier.

In another embodiment, the study-level image classifier may include two separate image level classifiers, wherein a first image level classifier receives two CC (i.e., CC L and CC R) MG images and the second image level classifier receives two MLO (i.e., MLO L and MLO R) MG images. Further, the study-level image classifier may include an image level classifier for each one of the four input images.

Embodiments of the present invention may be configured to output a prediction for the entire study, wherein the prediction may be representative of a benign or a malignant diagnosis. The system may also be configured to output a prediction for the left breast or the right breast. The system may also be configured to sort the results according to the Breast Imaging Reporting and Data System (BI-RADS), which sorts the results into categories numbered zero (0) through six (6). The system may also be configured to process the image data for each side separately and then combine the results through average or max operations. An image classifier of the system may be pre-trained to produce per-image diagnosis to improve training speed.

Further, embodiments of the present invention provide a diagnosis model that produces the overall diagnosis for the patient based on output data from the study-level image classifier.

The present invention will now be described in detail with reference to the Figures.

FIG. 1 depicts a block diagram of a distributed data processing environment 100 for annotating MG images, in accordance with an embodiment of the present invention. FIG. 1 provides only an illustration of one embodiment of the present invention and does not imply any limitations with regard to the environments in which different embodiments may be implemented. In the depicted embodiment, distributed data processing environment 100 includes computing device 120, server 125, database 124, and image sensor 130 interconnected over network 110. Network 110 operates as a computing network that can be, for example, a local area network (LAN), a wide area network (WAN), or a combination of the two, and can include wired, wireless, or fiber optic connections. In general, network 110 can be any combination of connections and protocols that will support communications between computing device 120, server 125, database 124, and image sensor 130. Distributed data processing environment 100 may also include additional servers, computers, sensors, or other devices not shown.

Computing device 120 operates to execute at least a part of a computer program for projecting MG image annotations onto MRI images and performing a diagnostic assessment. In an embodiment, computing device 120 may be communicatively coupled with image sensor 130 or image sensor 130 may be one of computing device 120 components. Computing device 120 be configured to send and/or receive data from network 110 and image sensor 130. In some embodiments, computing device 120 may be a management server, a web server, or any other electronic device or computing system capable of receiving and sending data. In some embodiments, computing device 120 may be a laptop computer, tablet computer, netbook computer, personal computer (PC), a desktop computer, a smart phone, or any programmable electronic device capable of communicating with database 124, server 125 via network 110. Computing device 120 may include components as described in further detail in FIG. 8.

Computing device 120 may also be configured to receive, store, and process images captured on image sensor 130. For example, computing device 120 may be communicatively coupled to image sensor 130 and receive, via a communications link, data corresponding to images captured by image sensor 130. Computing device 120 may be configured to store the image data in memory of computing device 120 or transmit the image data to database 124 or server 125 via network 110. The image data may be processed by one or more processors of computing device 120 or by one or more processors associated with server 125 in a cloud computing network.

Database 124 operates as a repository for data flowing to and from network 110. Examples of data include image data, annotated image data, user data, device data, network data, and data corresponding to images captured by image sensor 130. A database is an organized collection of data. Database 124 can be implemented with any type of storage device capable of storing data and configuration files that can be accessed and utilized by computing device 120, such as a database server, a hard disk drive, or a flash memory. In an embodiment, database 124 is accessed by computing device 120 to store data corresponding to images captured by image sensor. In another embodiment, database 124 is accessed by computing device 120 to access annotated image data, user data, device data, network data, and data corresponding to images captured by image sensor 130. In another embodiment, database 124 may reside elsewhere within distributed network environment 100 provided database 124 has access to network 110.

Server 125 can be a standalone computing device, a management server, a web server, or any other electronic device or computing system capable of receiving, sending, and processing data and capable of communicating with computing device 120 via network 110. In other embodiments, server 125 represents a server computing system utilizing multiple computers as a server system, such as a cloud computing environment. In yet other embodiments, server 125 represents a computing system utilizing clustered computers and components (e.g., database server computers, application server computers, etc.) that act as a single pool of seamless resources when accessed within distributed data processing environment 100. Server 125 may include components as described in further detail in FIG. 8.

Figure 2:
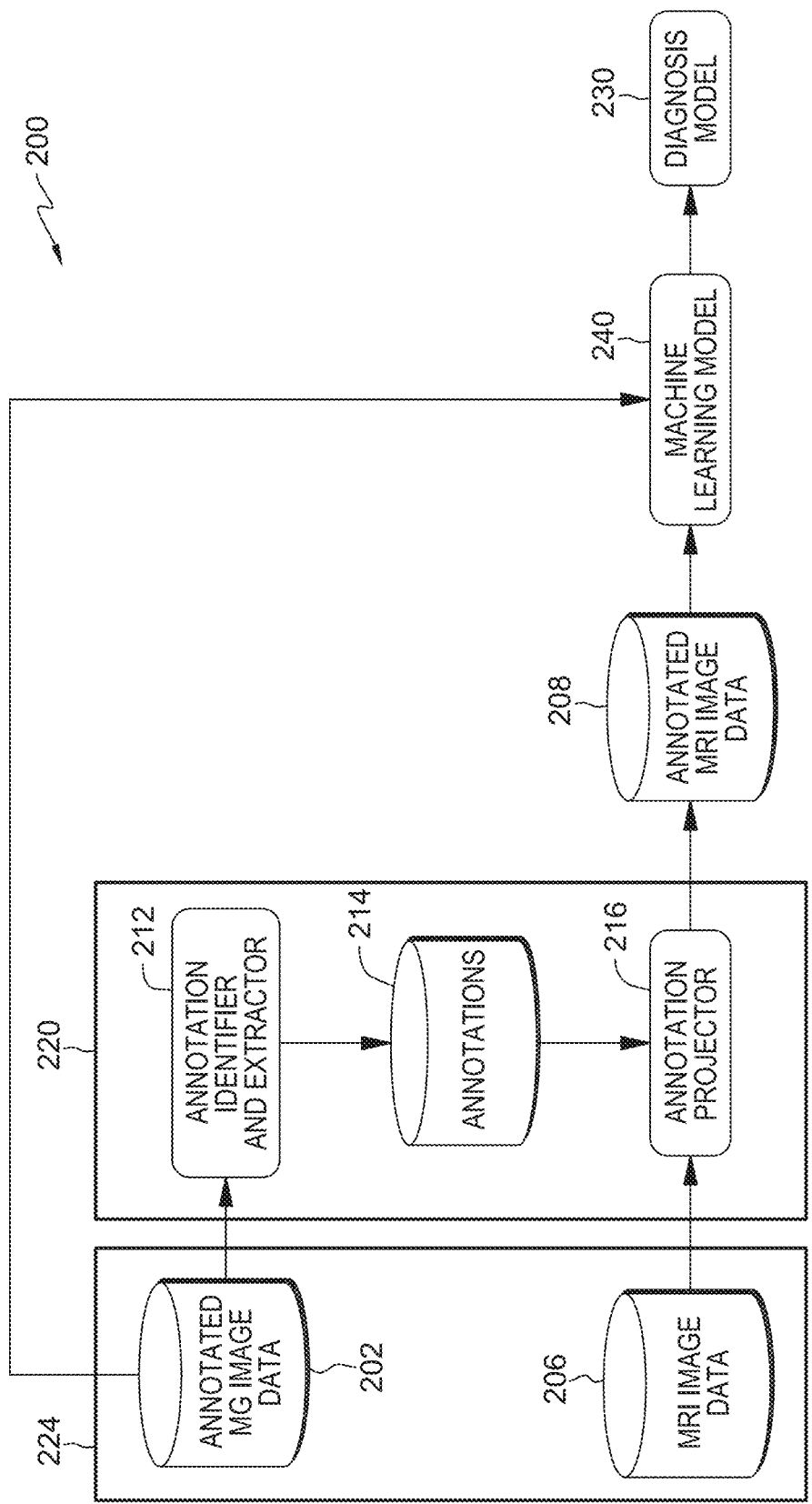
FIG. 2 depicts an architecture diagram of a study-level image model for annotating MRI images to perform a diagnostic assessment, in accordance with an embodiment of the present invention.

While the foregoing describes, and FIG. 2 illustrates, implementation of a study-level image model 200, the present disclosure is not limited thereto. In at least some embodiments, the model 200 may implement a trained component or trained model configured to perform the processes described above with respect to the study-level image model 200. The trained component may include one or more machine learning models 240, including but not limited to, one or more classifiers, one or more neural networks, one or more probabilistic graphs, one or more decision trees, and others. In other embodiments, the trained component may include a rules-based engine, one or more statistical-based algorithms, one or more mapping functions or other types of functions/algorithms to determine whether a natural language input is a complex or non-complex natural language input. In some embodiments, the trained component may be configured to perform binary classification, where the natural language input may be classified into one of two classes/categories. In some embodiments, the trained component may be configured to perform multiclass or multinomial classification, where the natural language input may be classified into one of three or more classes/categories. In some embodiments, the trained component may be configured to perform multi-label classification, where the natural language input may be associated with more than one class/category.

Various machine learning techniques may be used to train and operate trained components to perform various processes described herein. Models may be trained and operated according to various machine learning techniques. Such techniques may include, for example, neural networks (such as deep neural networks and/or recurrent neural networks), inference engines, trained classifiers, etc. Examples of trained classifiers include Support Vector Machines (SVMs), neural networks, decision trees, AdaBoost (short for "Adaptive Boosting") combined with decision trees, and random forests. Focusing on SVM as an example, SVM is a supervised learning model with associated learning algorithms that analyze data and recognize patterns in the data, and which are commonly used for classification and regression analysis. Given a set of training examples, each marked as belonging to one of two categories, an SVM training algorithm builds a model that assigns new examples into one category or the other, making it a non-probabilistic binary linear classifier. More complex SVM models may be built with the training set identifying more than two categories, with the SVM determining which category is most similar to input data. An SVM model may be mapped so that the examples of the separate categories are divided by clear gaps. New examples are then mapped into that same space and predicted to belong to a category based on which side of the gaps they fall on. Classifiers may issue a "score" indicating which category the data most closely matches. The score may provide an indication of how closely the data matches the category.

In order to apply the machine learning techniques, the machine learning processes themselves need to be trained. Training a machine learning component requires establishing a "ground truth" for the training examples. In machine learning, the term "ground truth" refers to the accuracy of a training set's classification for supervised learning techniques. Various techniques may be used to train the models including backpropagation, statistical learning, supervised learning, semi-supervised learning, stochastic learning, or other known techniques.

FIG. 2 depicts an architecture diagram of study-level image model 200 for annotating MRI images to perform a diagnostic assessment, in accordance with an embodiment of the present invention. Model 200 may include a machine learning model 240 configured to receive annotated MRI image data 208 and/or annotated MG image data 202 from image database 224. Annotated MRI image data 202 may be generated by computing device 220 including one or more processors configured for identifying and extracting annotations (e.g., using Annotation Identifier and Extractor 212). Computing device 220 (e.g., described in FIG. 1 as computing device 120) may include one or more processors configured for projecting or mapping (e.g., using Annotation Projector 216) one or more annotations 214 to MRI images represented by MRI image data 206. Further, computing device 220 may include one or more processors configured for generating annotated MRI image data 208 based on the MRI image data 206 and the one or more annotations 214 identified and extracted from annotated MG images represented in the annotated MG image data 202.

In an embodiment, annotation projector 216 may be configured to apply a lesion segmentation algorithm to generate annotated MRI image data 208. For example, once the breast side having the abnormality or lesion is identified in the MG image, the one or more processors (e.g., annotation projector 216) may be configured to automatically locate the most important image slices with the identified breast side in the MRI image data representing the MRI images. Further, the one or more processors may be configured to locate the relevant quadrant area in the relevant MRI image slices using the found breast quadrant in the MG images. The one or more processors (e.g., annotation projector 216) may be further configured to apply a lesion segmentation algorithm using only the found relevant MRI image slices and area in the MRI image data representing the MRI images. As a result, the annotation projector 216 may generate annotated MRI image data including the MRI images and annotations corresponding to the abnormality identified in the MG image data.

Machine learning model 240 may be configured to receive multiple input images and produce model output data as feature vectors corresponding to each image and transmit the model output data to a series of fully connected layers. The output data from the fully connected layers may be representative of a classification for a full study. In other words, if the study is a breast cancer diagnosis study for a specific patient, model output data for the study may be a classification that is one of either a normal, a benign, or a malignant diagnosis for the patient. This model output data may be in the form of a confidence score or probability for each classification representing the likelihood of a diagnosis corresponding to a normal, benign, and malignant classification.

In an embodiment, model 200 may include image database 224 configured to store, receive, and provide image data to and from components within model 200. For example, image database 224 may include annotated MG image data 202 and MRI image data 206 captured by image sensor 130 via computing device 120, in which image database 224 correlates to database 124 in FIG. 1.

In an embodiment, machine learning model 240 may be modified to include two separate image-level classifiers, e.g., one taking two bilateral CC images and the other taking two bilateral MLO images, or the left and right images, or a separate image-level classifier for each input image.

In an embodiment, annotations 214 may be provided to annotation projector 216 to generate annotated MRI image data 208. Annotations 214 may include data corresponding to information gathered about annotated MG image data 208 that may be provided to machine learning model 240 during training. Information relating to annotations 214 are made or provided by medical professionals or a computer program by appending relevant diagnostic information to be associated with the MG image.

In an embodiment, model 200 may include diagnosis model 230 configured to receive model output data from machine learning model 240 to produce an overall diagnosis for the study. For example, model output data from machine learning model 240 may be received at diagnosis model 230 to generate diagnosis data associated with a confidence score. In an embodiment, machine learning model 240 may be configured to receive annotated MG image data 202 produce first model output data, which when processed by diagnosis model 230 produces first diagnosis data corresponding to a first confidence score. In another embodiment, machine learning model 240 may be configured to receive annotated MRI image data 208 to produce second model output data, which, when processed by diagnosis model 230, produces second diagnosis data corresponding to a second confidence score, wherein the second confidence score is greater than the first confidence score, indicating a more accurate diagnosis. Alternatively, a second confidence score that is greater than a first confidence score may indicate a less accurate diagnosis, depending on the parameters of the study.

In another embodiment, machine learning model 240 may be pre-trained to produce per-image diagnoses to improve training speed.

Diagnosis model 230 may be implemented as any type of neural network that accepts time-series inputs of arbitrary length, such as a recurrent neural network ("RNN"), a long short-term memory ("LSTM"), or temporal convolution network ("TCN"). Diagnosis model 230 may also be implemented as an ensemble classifier, such as random forest, that takes the multiple predictions produced by machine learning model 240 described above and combines the predictions into a final diagnosis for the patient.

Figure 3:
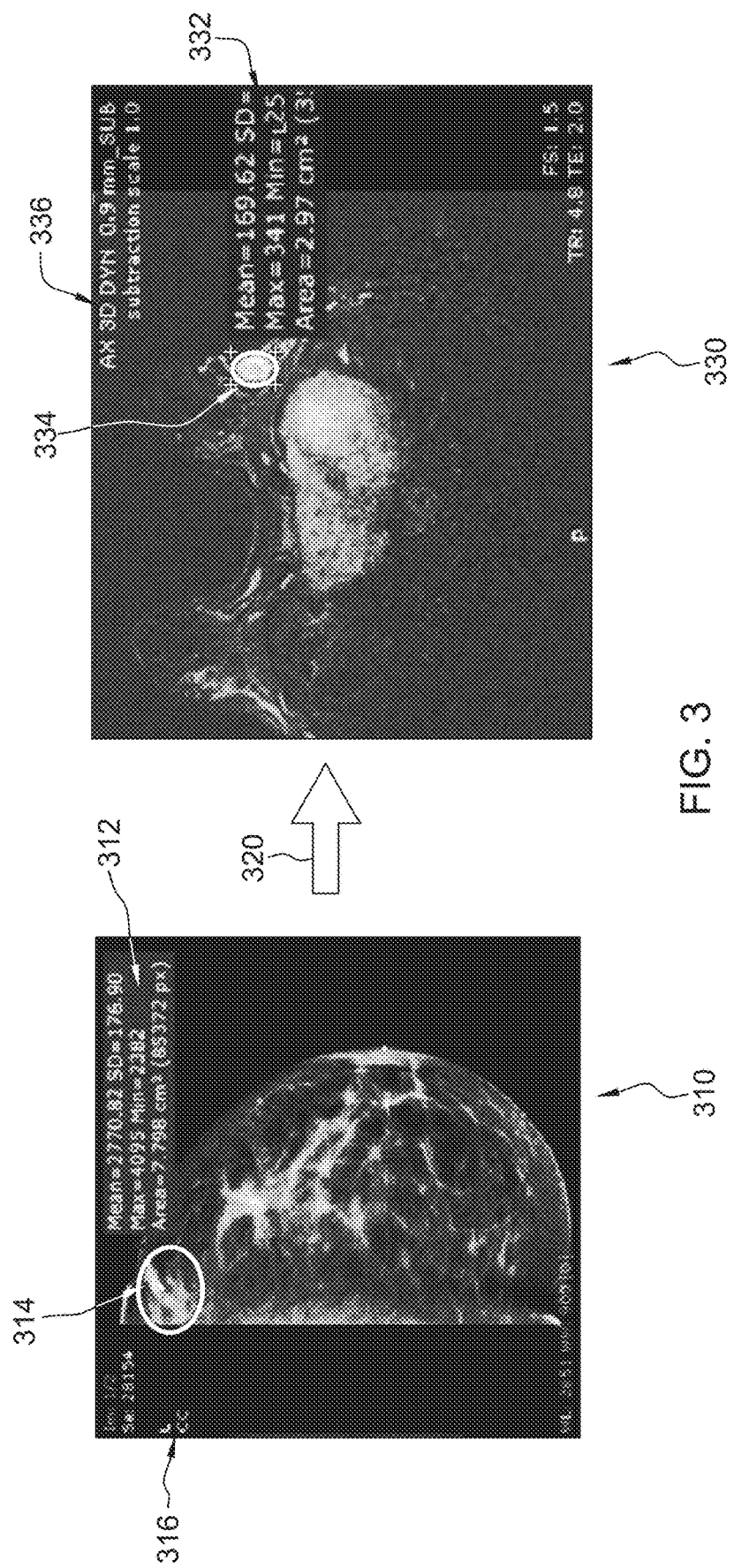
FIG. 3 depicts a set of annotated images, in accordance with an embodiment of the present invention.

FIG. 3 depicts a set of annotated images, in accordance with an embodiment of the present invention.

In an embodiment, one or more processors associated with computing device 120 may be configured to receive MG image data representing one or more annotated images 310 of a patient breast. The one or more processors may be configured to identify one or more MG annotations 312, 314 in the one or more annotated MG images, wherein the one or more MG annotations 312, 314 may represent an abnormality at a first location in the one or more annotated MG images 310. The one or more annotated MG images 310 may be of one of one or more view types, which may be identified by a view type annotation. In this example, view type annotation 316 is L CC corresponding to a craniocaudal view of the left breast. The view type for a MG image may be a 2-dimensional (2D) view and the view type for an MRI image may be a 3-dimensional (3D) view.

As described above herein, the one or more processors may be configured for determining a breast side and a quadrant of the patient breast based on the first location in the one or more annotated MG images 310. A breast side (e.g., left "L" side or a right "R" side) and a quadrant (e.g., upper-outer "UO", lower-outer "LO", upper-inner "UI", and lower-inner "LI") may be used to describe the location of a lesion or abnormality. The one or more annotations illustrated in the one or more MRI images 330 may be generated by the one or more processors by mapping 320 the one or more MG annotations 312, 314 to the second location of the corresponding breast side and quadrant of the one or more MRI images 330 represented in the MRI image data. Mapping 320 the one or more MG annotations 312, 314 to the one or more MRI images 330 at the corresponding location of the abnormality results in generating one or more MRI annotations 332, 334.

Further, the one or more processors associated with computing device 120 may be configured to receive MRI image data representing one or more MRI images 330 of the patient breast. The one or more processors may be configured to generate annotated MRI image data using the MRI image data and the one or more MG annotations 312, 314 identified in the one or more annotated MG images 310. The annotated MRI image data may include one or more MRI annotations 332, 334 representing the abnormality at a second location based at least in part on the first location. For example, the one or more MRI images 330 is of a second view type identified by view type annotation 336 is AX 3D DYN 0.9 mm_SUB corresponding to an axial 3D dynamic view with a scale of 0.9 mm.

The second location of the abnormality, visually identifiable by MRI annotation 334, may be determined by converting the 2D coordinate information of the first location of the abnormality, identified by MG annotation 314, to 3D coordinate information.

Other annotation schema may be used to annotate MG images to describe the mass, calcification, and other imaging observations of an abnormality. For example, the mass of the abnormality may be annotated to describe the density, margin, shape, size, and count/number of the abnormality. The calcification of the abnormality may be annotated to describe the count/number, distribution, and stability of the abnormality. Other imaging observations may include architectural, distortion, associated findings, overall breast appearance, composition, or special cases. Imaging observations may be ascertained based on the mass, calcification, and other imaging observations, whereas the anatomic entity may be determined as a result of also considering the location and laterality of the abnormality and its associated characteristics.

Figure 4:
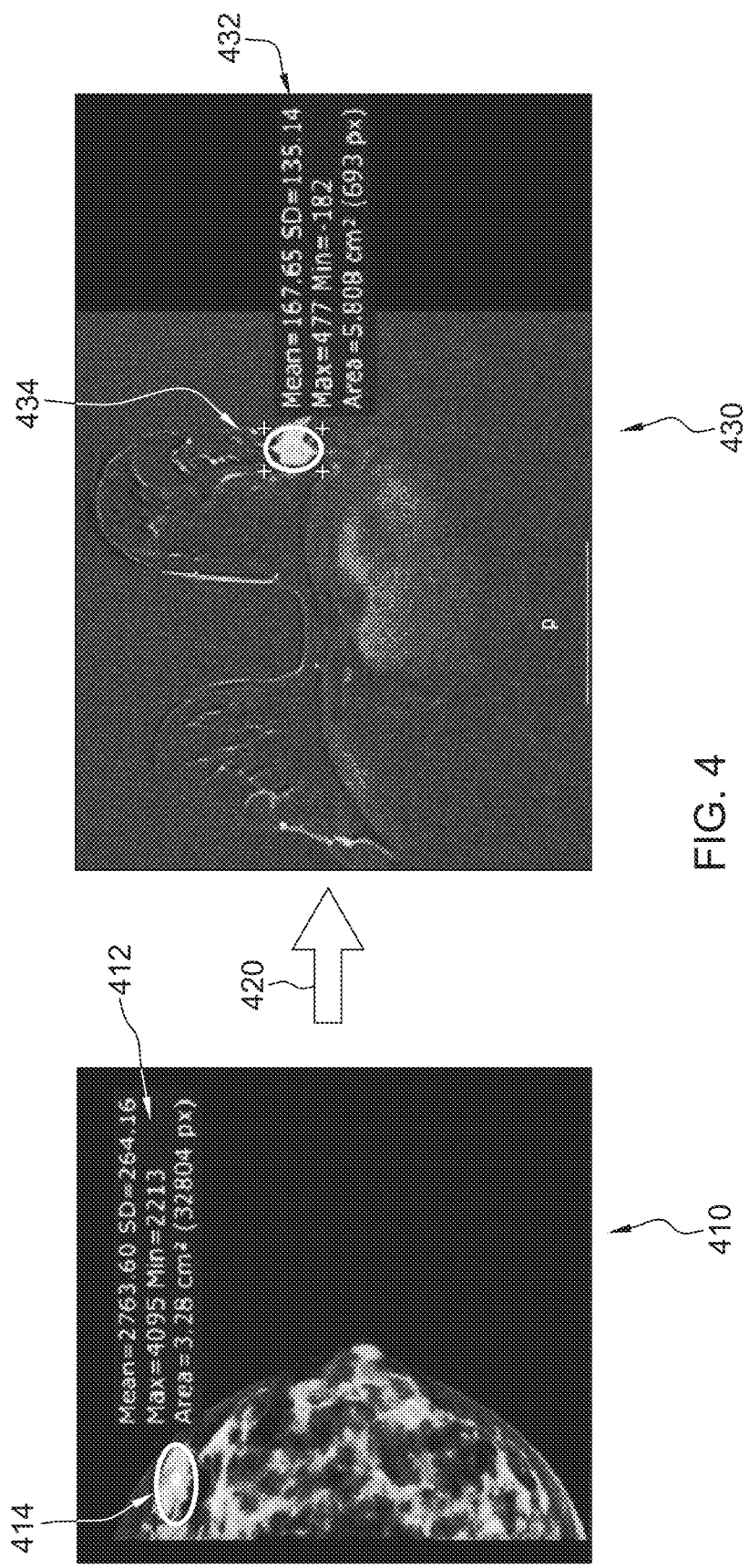
FIG. 4 depicts another set of annotated images, in accordance with an embodiment of the present invention.

FIG. 4 depicts another set of annotated images, in accordance with an embodiment of the present invention.

In an embodiment, one or more processors associated with computing device 120 may be configured to receive MG image data representing one or more annotated images 410 of a patient breast. The one or more processors may be configured to identify one or more MG annotations 412, 414 in the one or more annotated MG images, wherein the one or more MG annotations 412, 414 may represent an abnormality at a first location in the one or more annotated MG images 410. The one or more annotated MG images 410 may be of one of one or more view types, which may be identified by a view type annotation, not shown in this example.

Further, the one or more processors associated with computing device 120 may be configured to receive MRI image data representing one or more MRI images 430 of the patient breast. The one or more processors may be configured to generate annotated MRI image data using the MRI image data and the one or more MG annotations 412, 414 identified in the one or more annotated MG images 410. The one or more processors may generate annotated MRI image data by mapping 420 the one or more MG annotations 412, 414 to the one or more MRI images 430. Mapping annotations may include identifying the one or more annotations, extracting the one or more annotations, and applying the one or more annotations to a location consistent with the location from which the one or more annotations were extracted from. The annotated MRI image data may include one or more MRI annotations 432, 434 representing the abnormality at a second location based at least in part on the first location.

Figure 5:
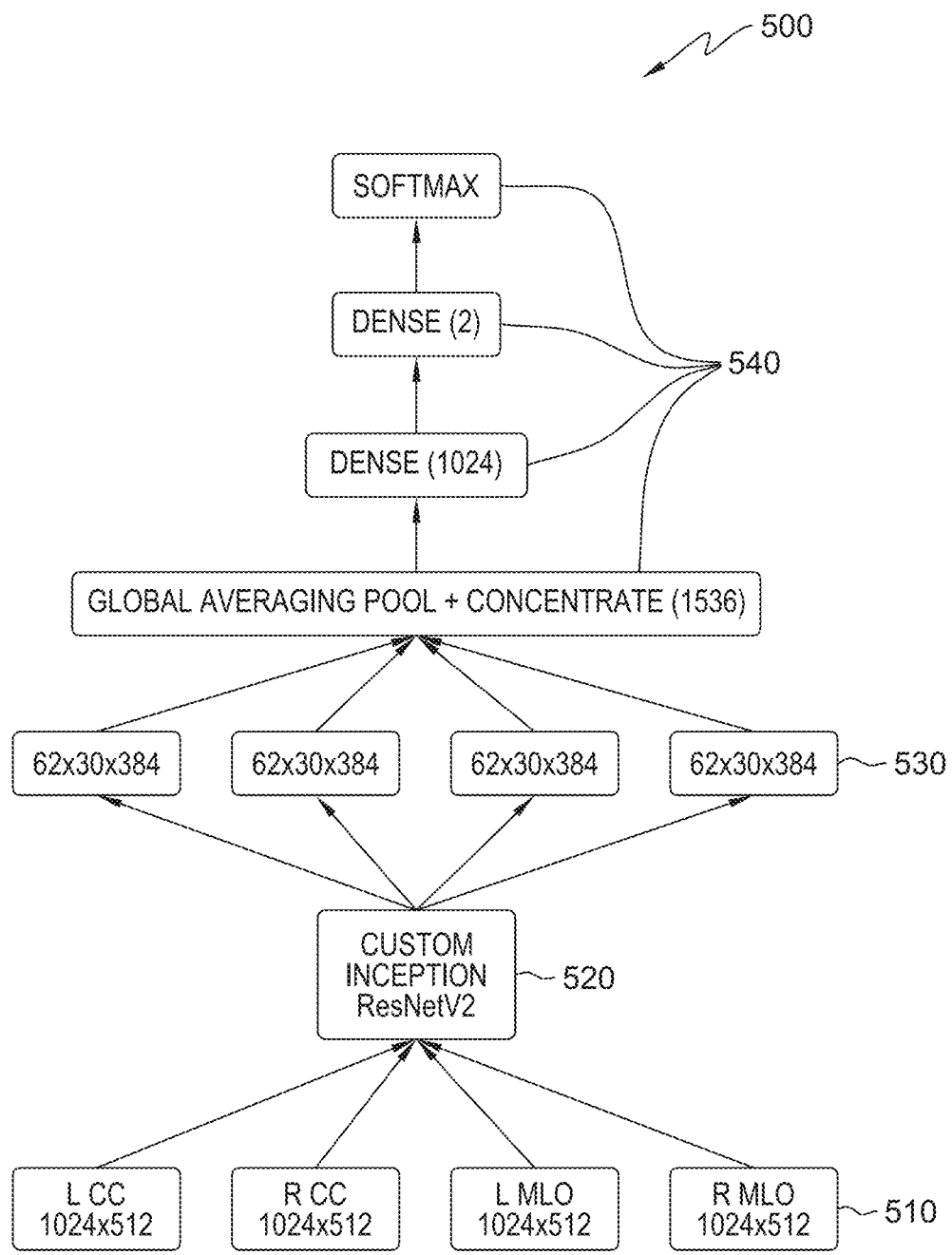
FIG. 5 depicts a flow chart of a machine learning model used for performing a diagnostic assessment using annotated images, in accordance with an embodiment of the present invention.

FIG. 5 depicts a flow chart of machine learning model 500 used for performing a diagnostic assessment using annotated images, in accordance with an embodiment of the present invention.

In an embodiment, machine learning model 500 may receive MRI image data 510 corresponding to MRI images and/or annotated MRI images captured during a patient diagnostic exam. Machine learning model 500 may include an image classifier (e.g., Custom Inception ResNetV2) 520 configured to process MRI image data 510 and generate model output data 530 representing features of the MRI image data 510. Model output data 530 may also be a 2-D feature map having 62×30×384 for each image.

In an embodiment, result combination network 540 may be configured to combine the model output data 530 to generate a binary probability. Further, result combination network 540 may be configured to performing global average pooling by taking 3-D feature vectors and reduce the 3-D feature vectors to one dimension by averaging the 62×30×384-dimensional feature vector for each image and concatenating the feature vectors to a one-dimensional feature vector of 1536. Result combination network 540 may also include a dense layer that is a fully connected layer where each input from the concatenated layer would connect to the fully connected layer. Softmax takes the output from the fully connected layer and generates a binary probability. A binary probability may be determined using the Softmax function, as described herein. Machine learning model 500 may also be configured to output a prediction for each image view provided in MRI image data 510. Alternatively, the Softmax function may be configured to generate a 6-dimensional vector consistent with BIRADs protocols, wherein the 6-dimensional vector may include a ranking between zero (0) and six (6) depending on the severity of the diagnosis in line with the BIRADS protocols.

Figure 6:
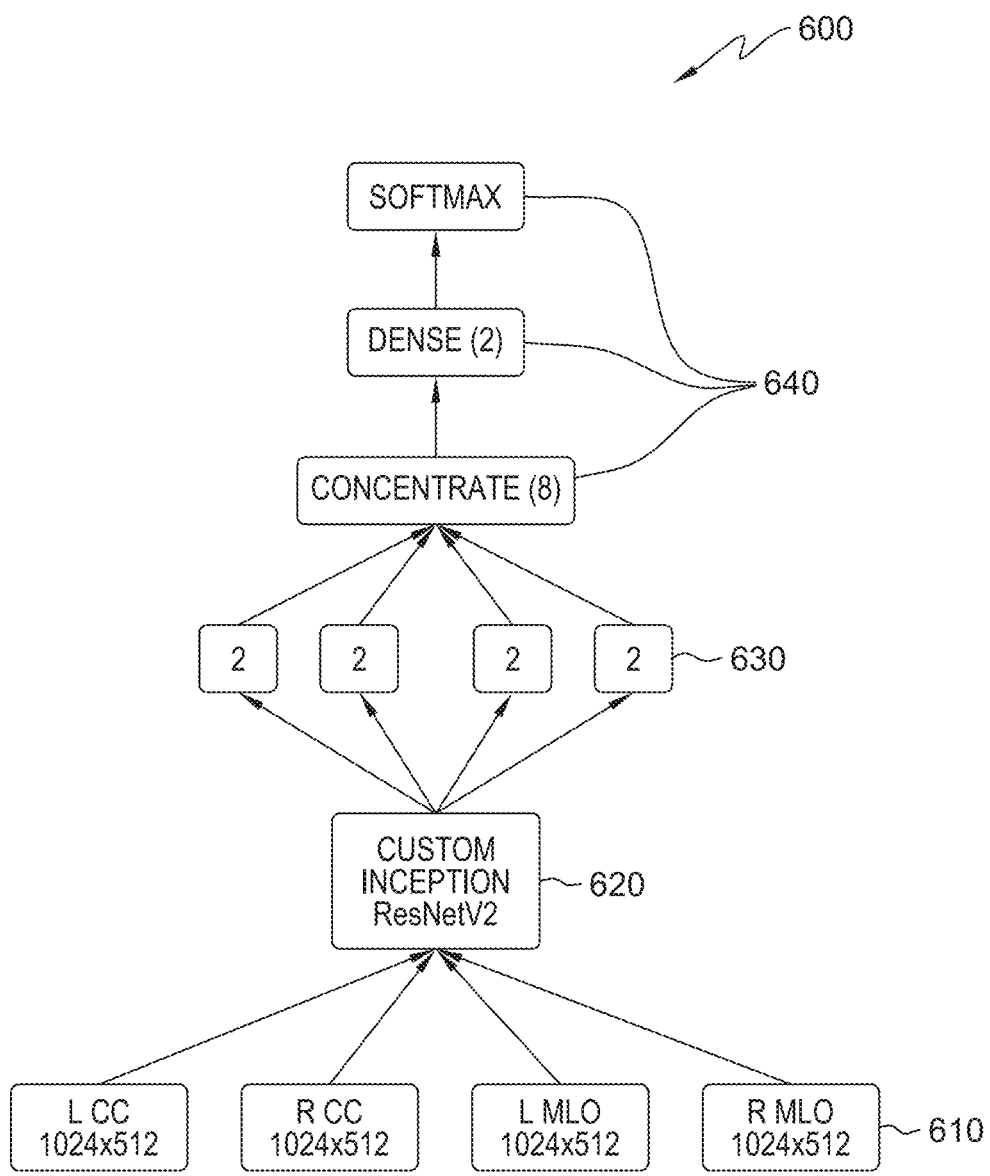
FIG. 6 depicts a flow chart of another machine learning model used for performing a diagnostic assessment using annotated images, in accordance with an embodiment of the present invention.

FIG. 6 depicts a process flow of machine learning model 600 used for performing a diagnostic assessment using annotated images, in accordance with an embodiment of the present invention.

In an embodiment, machine learning model 600 may include an image level classifier (e.g., Custom Inception ResNetV2) 620 configured to process MRI image data 610 and generate model output data 630 representing features of the MRI image data 610. Model output data 630 may also be a 2-D feature map providing a classification for each image, wherein the classification may be one of various diagnoses. For example, model output data 630 may provide a classification for each image corresponding to a benign diagnosis or a malignant diagnosis. Result combination network 640 may be configured to receive model output data 630 and may then be configured to concatenate and reduce model output data 630 to a single feature vector by a dense function, which may then be provided to a Softmax function as described above.

Figure 7:
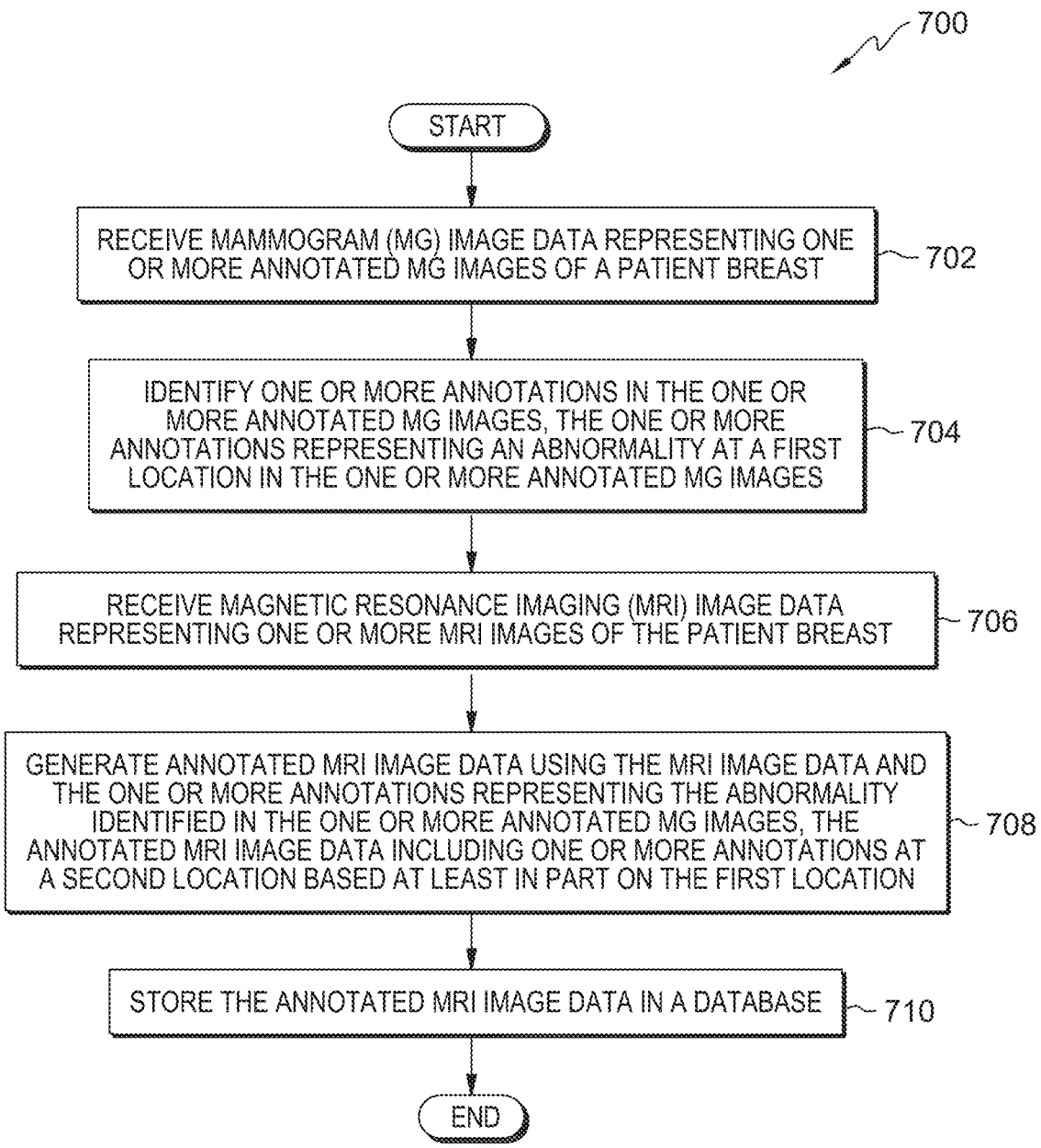
FIG. 7 depicts a flow chart of steps of a computer-implemented method for annotating MRI images, in accordance with an embodiment of the present invention.

FIG. 7 depicts a flow chart of a computer-implemented method 700 for annotating MRI images, in accordance with an embodiment of the present invention.

In an embodiment, computer-implemented method 700 may include one or more processors configured to receive 702 annotated MG image data 202 representing one or more annotated MG images of a patient breast. The one or more processors may be associated with computing device 120, 220 and be configured to receive 702 MG image data representing one or more annotated MG images of a patient breast from database 124 via network 110.

Further, method 700 may include one or more processors configured to identify 704 one or more annotations in the one or more annotated MG images, the one or more annotations representing an abnormality at a first location in the one or more annotated MG images. Annotations may be identified as text or numerical characters displayed on the one or more annotated MG images. The annotations may represent an abnormality or lesion identified within the one or more MG images. The annotations may include geometric information describing the location or characteristic of the abnormality or lesion. The annotation may also identify a view type of the one or more MG images or identify a particular region of the patient breast where the abnormality or lesion is located. For example, one or more annotations may include a breast side and view type (e.g., L CC—left craniocaudal view) of the patient breast. Further, the one or more annotations may include a quadrant (e.g., upper-outer "UO", lower-outer "LO", upper-inner "UI", and lower-inner "LI") used to describe a region of a patient breast including the lesion or abnormality.

Further, method 700 may further include one or more processors configured to receive 706 MRI image data representing one or more MRI images of the patient breast. The one or more processors may be configured to generate annotated MRI image data using the MRI image data and the one or more MG annotations identified in the one or more annotated MG images. The annotated MRI image data may include one or more MRI annotations representing the abnormality at a second location based at least in part on the first location. The second location of the abnormality, identified by MRI annotation 334, may be determined by converting the 2D coordinate information of the first location of the abnormality, identified by MG annotation 314, to 3D coordinate information. For example, if the first location is determined to be at X coordinate and Y coordinate in a 2D image map, then the second location may be determined to be at X' coordinate, Y' coordinate, and Z coordinate in a 3D image map, wherein X' is the 3D representation of the X coordinate, the Y' coordinate is the 3D representation of the Y coordinate, and the Z coordinate represents the added dimensional coordinate from mapping the 2D coordinate of the first location to the 3D coordinate of the second location.

The one or more MRI images may be of a second view type corresponding to a first view type including information representing the image scale.

Further, method 700 may further include one or more processors configured to generate 708 annotated MRI image data using the MRI image data and the one or more annotations identified in the one or more annotated MG images, the annotated MRI image data including one or more annotations representing the abnormality at a second location based at least in part on the first location.

Further, method 700 may further include one or more processors configured to store 710 the annotated MRI image data in a database.

Figure 8:
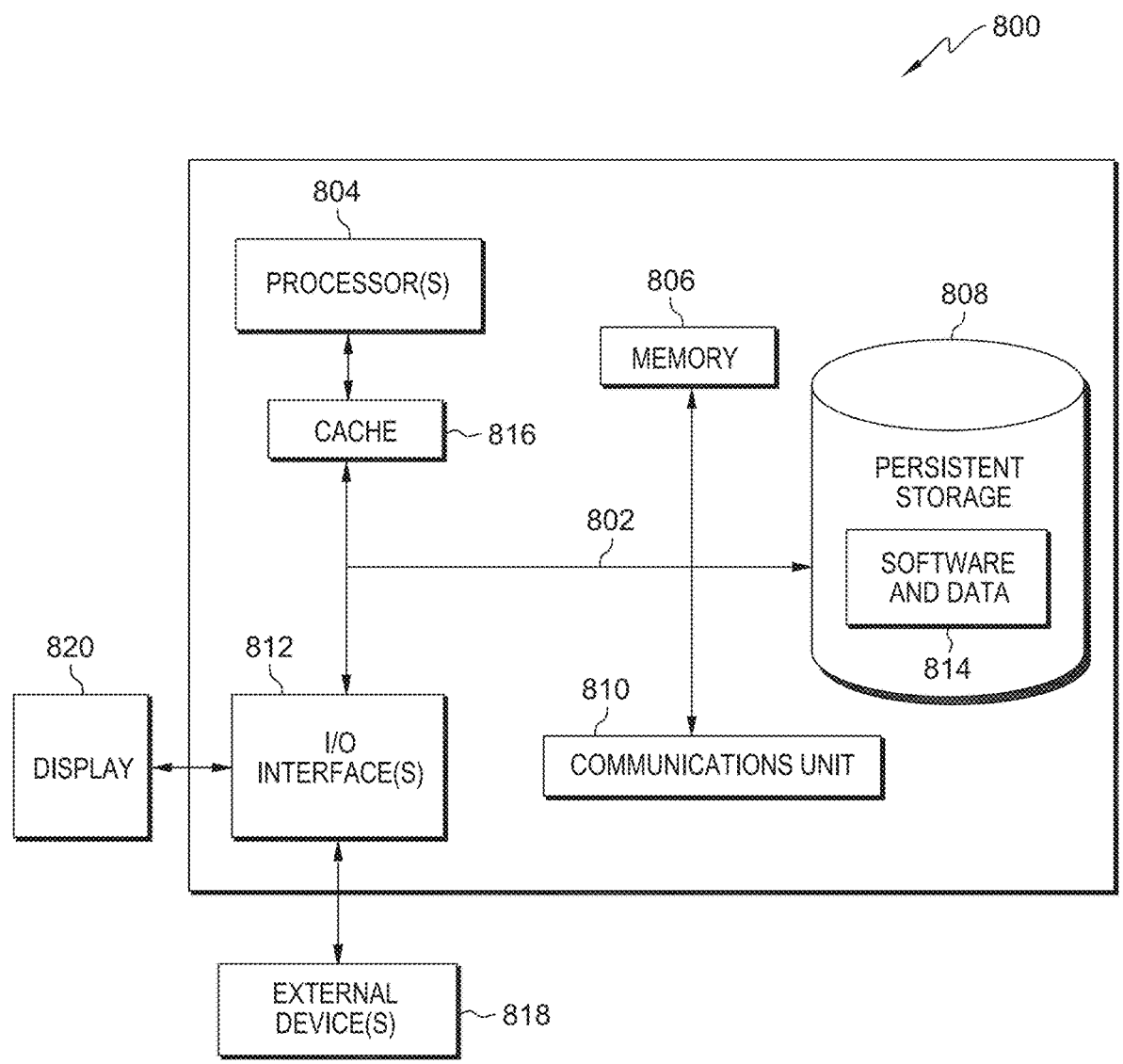
FIG. 8 depicts a block diagram of a computing device of the distributed data processing environment of FIG. 1, in accordance with an embodiment of the present invention.

FIG. 8 depicts a block diagram of a computing device of distributed computing environment, in accordance with an embodiment of the present invention. FIG. 8 depicts a block diagram of computing device 800 suitable for server(s) 125 and computing device 120, in accordance with an illustrative embodiment of the present invention. It should be appreciated that FIG. 8 provides only an illustration of one implementation and does not imply any limitations with regard to the environments in which different embodiments may be implemented. Many modifications to the depicted environment may be made.

Computing device 800 includes communications fabric 802, which provides communications between cache 816, memory 806, persistent storage 808, communications unit 810, and input/output (I/O) interface(s) 812. Communications fabric 802 can be implemented with any architecture designed for passing data and/or control information between processors (such as microprocessors, communications and network processors, etc.), system memory, peripheral devices, and any other hardware components within a system. For example, communications fabric 802 can be implemented with one or more buses or a crossbar switch.

Memory 806 and persistent storage 808 are computer readable storage media. In this embodiment, memory 806 includes random access memory (RAM). In general, memory 806 can include any suitable volatile or non-volatile computer readable storage media. Cache 816 is a fast memory that enhances the performance of computer processor(s) 804 by holding recently accessed data, and data near accessed data, from memory 806.

Programs may be stored in persistent storage 808 and in memory 806 for execution and/or access by one or more of the respective computer processors 804 via cache 816. In an embodiment, persistent storage 808 includes a magnetic hard disk drive. Alternatively, or in addition to a magnetic hard disk drive, persistent storage 808 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 808 may also be removable. For example, a removable hard drive may be used for persistent storage 808. Other examples include optical and magnetic disks, thumb drives, and smart cards that are inserted into a drive for transfer onto another computer readable storage medium that is also part of persistent storage 808.

Communications unit 810, in these examples, provides for communications with other data processing systems or devices. In these examples, communications unit 810 includes one or more network interface cards. Communications unit 810 may provide communications through the use of either or both physical and wireless communications links. Programs, as described herein, may be downloaded to persistent storage 808 through communications unit 810.

I/O interface(s) 812 allows for input and output of data with other devices that may be connected to computing device 120. For example, I/O interface 812 may provide a connection to external devices 818 such as image sensor 130, a keyboard, a keypad, a touch screen, and/or some other suitable input device. External devices 818 can also include portable computer readable storage media such as, for example, thumb drives, portable optical or magnetic disks, and memory cards. Software and data 814 used to practice embodiments of the present invention can be stored on such portable computer readable storage media and can be loaded onto persistent storage 808 via I/O interface(s) 812. I/O interface(s) 812 also connect to a display 820.

Display 820 provides a mechanism to display data to a user and may be, for example, a computer monitor.

Software and data 814 described herein is identified based upon the application for which it is implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a computer-implemented method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of computer-implemented methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
receiving, by one or more processors, mammogram (MG) image data representing one or more annotated MG images of a patient breast;
identifying, by one or more processors, one or more MG annotations in the one or more annotated MG images, the one or more MG annotations representing an abnormality at a first location in the one or more annotated MG images;
receiving, by one or more processors, MRI image data representing one or more MRI images of the patient breast;
automatically selecting, by one or more processors, a subset of the MRI image data based on extracting, from the one or more annotated MG images, an identification of breast side of the patient and a quadrant of the abnormality at the first location;
generating, by one or more processors, annotated MRI image data using the subset of the MRI image data and the one or more MG annotations identified in the one or more annotated MG images, the annotated MRI image data including one or more MRI annotations representing the abnormality at a second location based at least in part on the first location; and
storing, by one or more processors, the annotated MRI image data in a database.

2. The computer-implemented method of claim 1, wherein each of the one or more annotated MG images is of a view selected from the group consisting of: craniocaudal (CC) and mediolateral oblique (MLO).

3. The computer-implemented method of claim 1, wherein the one or more MRI images comprise a plurality of image slices including one or more image slices having the abnormality.

4. The computer-implemented method of claim 3, further comprising:
determining, by one or more processors, the breast side of the patient and the quadrant of the patient breast based on the first location in the one or more annotated MG images.

5. The computer-implemented method of claim 1, wherein generating the annotated MRI image data comprises:
mapping, by one or more processors, the one or more MG annotations to the second location of the corresponding breast side and the quadrant of the MRI images represented in the MRI image data.

6. The computer-implemented method of claim 1, further comprising:
providing, by one or more processors, the annotated MRI image data to a supervised machine learning model; and
processing, by one or more processors, the annotated MRI image data with the one or more MRI annotations using the supervised machine learning model to generate output data corresponding to a diagnosis.

7. A computer program product comprising:
one or more computer readable storage media and program instructions collectively stored on the one or more computer readable storage media, the program instructions comprising:
program instructions to receive mammogram (MG) image data representing one or more annotated MG images of a patient breast;
program instructions to identify one or more MG annotations in the one or more annotated MG images, the one or more MG annotations representing an abnormality at a first location in the one or more annotated MG images;
program instructions receive MRI image data representing one or more MRI images of the patient breast;
program instructions to automatically select a subset of the MRI image data based on extracting, from the one or more annotated MG images, an identification of breast side of the patient and a quadrant of the abnormality at the first location;
program instructions to generate annotated MRI image data using the subset of the MRI image data and the one or more MG annotations identified in the one or more annotated MG images, the annotated MRI image data including one or more MRI annotations at a second location based at least in part on the first location, the one or more MRI annotations in the annotated MRI image data representing the abnormality; and
program instructions to store the annotated MRI image data in a database.

8. The computer program product of claim 7, wherein each of the one or more annotated MG images is of a view selected from the group consisting of: craniocaudal (CC) and mediolateral oblique (MLO).

9. The computer program product of claim 7, wherein the one or more MRI images comprise a plurality of image slices including one or more image slices having the abnormality.

10. The computer program product of claim 9, further comprising:
program instructions to determine the breast side of the patient and the quadrant of the patient breast based on the first location in the one or more annotated MG images.

11. The computer program product of claim 7, wherein the program instructions to generate the annotated MRI image data comprises:
program instructions to map the one or more MG annotations to the second location of the corresponding breast side and the quadrant of the MRI images represented in the MRI image data.

12. The computer program product of claim 7, further comprising:
program instructions to provide the annotated MRI image data to a supervised machine learning model; and
program instructions to process the annotated MRI image data with the one or more MRI annotations using the supervised machine learning model to generate output data corresponding to a diagnosis.

13. A computer system comprising:
one or more computer processors;
one or more computer readable storage media;
program instructions collectively stored on the one or more computer readable storage media for execution by at least one of the one or more processors, the program instructions comprising:
program instructions to receive mammogram (MG) image data representing one or more annotated MG images of a patient breast;

program instructions to identify one or more MG annotations in the one or more annotated MG images, the one or more MG annotations representing an abnormality at a first location in the one or more annotated MG images;

program instructions to receive MRI image data representing one or more MRI images of the patient breast;

program instructions to automatically select a subset of the MRI image data based on extracting, from the one or more annotated MG images, an identification of breast side of the patient and a quadrant of the abnormality at the first location;

program instructions to generate annotated MRI image data using the subset of the MRI image data and the one or more MG annotations identified in the one or more annotated MG images, the annotated MRI image data including one or more MRI annotations at a second location based at least in part on the first location, the one or more MRI annotations in the annotated MRI image data representing the abnormality; and program instructions to store the annotated MRI image data in a database.

14. The computer system of claim 13, wherein each of the one or more annotated MG images is of a view selected from the group consisting of: craniocaudal (CC) and mediolateral oblique (MLO).

15. The computer system of claim 14, wherein the one or more MRI images comprise a plurality of image slices including one or more image slices having the abnormality.

16. The computer system of claim 13, further comprising:
program instructions to determine the breast side of the patient and the quadrant of the patient breast based on the first location in the one or more annotated MG images.

17. The computer system of claim 13, wherein the program instructions to generate the annotated MRI image data comprises:
program instructions to map the one or more annotations to the second location of the corresponding breast side and the quadrant of the MRI images represented in the MRI image data.

18. The computer system of claim 13, further comprising:
program instructions to provide the annotated MRI image data to a supervised machine learning model; and
program instructions to process the annotated MRI image data with the one or more MRI annotations using the supervised machine learning model to generate output data corresponding to a diagnosis.

* * * * *